United States Patent
Hartmann et al.

(10) Patent No.: US 8,357,658 B2
(45) Date of Patent: *Jan. 22, 2013

(54) MEDICAMENT FOR TREATING PARKINSON'S DISEASE

(75) Inventors: Andréas Hartmann, Paris (FR); Anne-Marie Bonnet, Paris (FR); Michael Schüpbach, Paris (FR)

(73) Assignee: Assistance Publique—Hopitaux de Paris, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/667,468

(22) PCT Filed: Jul. 1, 2008

(86) PCT No.: PCT/FR2008/000938
§ 371 (c)(1), (2), (4) Date: Sep. 15, 2010

(87) PCT Pub. No.: WO2009/022068
PCT Pub. Date: Feb. 19, 2009

(65) Prior Publication Data
US 2011/0009330 A1    Jan. 13, 2011

(30) Foreign Application Priority Data

Jul. 2, 2007  (FR) .................................... 07 04754

(51) Int. Cl.
*A61K 35/64* (2006.01)
*A61P 25/16* (2006.01)

(52) U.S. Cl. ........ 514/17.7; 514/1.1; 514/17.4; 530/858

(58) Field of Classification Search .................. None
See application file for complete search history.

(56) References Cited

PUBLICATIONS

Clayton et al., Modified Rapid Venom Desensitization, 1993, Clinical Allergy 13:123-129.*

U.S. Appl. No. 12/667,471, filed Dec. 31, 2009, Hartmann, et al.
Krivolapov-Moscvin, Igor Vladimirovich "Apitoxinotherapy in the treatment of Parkinsosn's disease", The International Centre of Traditional & Alternative Medicine "API"—The Leading Apitherapeutical Department, XP-002470214, pp. 1-2, (Feb. 21, 2008).
Wulff, Heike et al., "Modulators of Small- and Intermediate-Conductance Calcium-Activated Potassium Channels and their Therapeutic Indications", Current Medicinal Chemistry, vol. 14, No. 13, XP-002470707, pp. 1437-1457, (Jun. 2007).
Liegeois, J.-F. et al., "Modulation of Small Conductance Calcium-Activated Potassium (SK) Channels: A New Challenge in Medicinal Chemistry", Current Medicinal Chemistry, vol. 10, No. 8, XP009078299, pp. 625-647, (Apr. 2003).
Dilly, Sebastien et al., "Identification of a pharmacophore of SKCa channel blockers", Journal of Enzyme Inhibition and Medicinal Chemistry, Taylor & Francis Group, vol. 20, No. 6, XP009085532, pp. 517-523, (Dec. 2005).
Lupu, Alexandra "Apitherapy—The Bee Venom Therapy", SOFTPEDIA, pp. 1-2, XP-002549609, (Aug. 15, 2006).
Hallworth, Nicholas E. et al., "Apamin-Sensitive Small Conductance Calcium-Activated Potassium Channels, Through their Selective Coupling to Voltage-Gated Calcium Channels, Are Critical Determinants of the Precision, Pace, and Pattern of Action Potential Generation in Rat Subthalamic Nucleus Neurons In Vitro", The Journal of Neurosicence, vol. 23, No. 20, XP-002268345,pp. 7525-7542, (Aug. 20, 2003).

* cited by examiner

*Primary Examiner* — John Ulm
(74) *Attorney, Agent, or Firm* — Albrecht Tousi & Farnum PLLC; Susan M. Dadio

(57) ABSTRACT

The invention relates to the manufacture of a unit dose of a medicament for relieving the symptoms and/or restoring and/or protecting the neurons of patients suffering from Parkinson's disease. According to the invention, apamine is used in an amount of between 1 and 10 micrograms inclusive, for the manufacture of a unit dose for subcutaneous injection, every one to six weeks, of a medicament for relieving the symptoms and/or restoring and/or protecting the neurons of patients suffering from Parkinson's disease. The invention finds use in particular in the field of pharmacy.

37 Claims, No Drawings

MEDICAMENT FOR TREATING PARKINSON'S DISEASE

The present application is a 35 U.S.C. §371 National Stage patent application of International patent application PCT/FR2008/000938, filed on Jul. 1, 2008, which claims priority to French patent application FR 0704754, filed on Jul. 2, 2007.

The invention relates to the use of apamin or of bee venom in the manufacture of a medicament for restoring and/or for protecting neurons, and/or for long-term symptomatic treatment, in Parkinson's disease.

Parkinson's disease is a disorder which affects the nerve cells, or neurons, in a part of the brain, the substantia nigra pars compacta, which controls muscle movement. In Parkinson's disease, the neurons, which produce dopamine, die or do not function normally.

However, it is, inter alia, the dopamine produced by the neurons which sends the signals that make it possible to initiate and coordinate movements.

The cause of the nerve cell damage is not known.

Parkinson's disease generally affects individuals approximately sixty years old, but can begin earlier.

Akinesia is the major symptom of Parkinson's disease. This symptom is defined principally as being a problem with initiating movement, which leads the patient to gradually decrease his or her motor activity. For several authors, the term akinesia is used more broadly, and also includes the decrease in amount of movement (hypokinesia), slowing down in the execution of movement (bradykinesia) and loss of the ability to execute automatic movements. Thus, Parkinsonian patients exhibit a characteristic increase in muscle tone ("cog-wheel" rigidity). Finally, resting tremors (4-8 Hz) are present in approximately ⅔ of cases. When the symptoms become amplified, individuals suffering from Parkinson's disease have difficulty in walking, speaking or in performing simple tasks. They may also have depressive disorders, sleep disorders, and also cognitive and dysautonomic disorders.

It is generally recognized that the symptoms of Parkinson's disease appear only when 50% of the nigral dopaminergic neurons are destroyed. In addition to these 50% of destroyed neurons, 15 to 20% are said to be silent, i.e. they remain morphologically intact but no longer produce dopamine or produce very little dopamine.

The medicaments currently used make it possible only to relieve, admittedly considerably, the symptoms of Parkinson's disease, but do not make it possible to stop the progression of the disease and even less to restore the function of the damaged neurons.

The medicaments currently used are principally L-dopa in its various forms, and also dopaminergic antagonists. L-dopa is converted to dopamine in dopaminergic neurons by dopa-decarboxylase. These medicaments produce a variety of peripheral side effects, in particular hypotension and nausea. More serious is the fact that, after 5 to 10 years of treatment, the pulsatility of the administration of these molecules in several intakes per day—in contrast with the constant release of physiological dopamine—induces motor fluctuations that are generally very incapacitating. Thus, it is important to note that these molecules act purely symptomatically and do not slow down the degenerative process.

The invention aims to overcome the drawbacks of the medicaments used in the treatment of Parkinson's disease by proposing a medicament which makes it possible not only to protect the undamaged neurons, but also to restore the function of the "silent" neurons while at the same time not causing the side effects due to the administration of L-dopa. Thus, in the shorter term, the invention should make it possible to obtain a long-lasting symptomatic effect.

To this effect, the invention proposes the use of apamin in an amount of between 1 and 10 micrograms, limits included, in the manufacture of a unit dose for subcutaneous injection, every one to six weeks, of a medicament for relieving the symptoms and/or restoring and/or protecting the neurons of patients suffering from Parkinson's disease.

Apamin is an 18 amino acid peptide of sequence: CNCKAPETAL CARRCQQH (SEQ ID No. 1).

Apamin is capable of crossing the blood-brain barrier.

It is also a blocker of SK3 sub-unit potassium channels, expressed by the dopaminergic neurons of the mesencephalon.

The amount of apamin to be used for manufacturing a unit dose, to be injected subcutaneously, of the medicament for relieving the symptoms and/or restoring and/or protecting the neurons of patients suffering from Parkinson's disease, depends on the patient himself or herself, and in particular on the body weight thereof.

Thus, this amount is between 1 and 10 micrograms, preferably between 2 and 5 micrograms, and more preferably between 3 and 3.5 micrograms.

The frequency of injection of this unit dose will also depend on the patient and on the stage of the disease of said patient.

Thus, at the beginning of treatment, one injection every week is appropriate. Then, depending on the progression of the patient's condition, the frequency of injections may be one injection every six weeks.

In any event, this is a considerable advantage compared with L-dopa, which must be administered daily and several times a day.

In one preferred embodiment of the use of apamin in the manufacture of a unit dose, to be injected subcutaneously every one to six weeks, of a medicament for relieving the symptoms and/or restoring and/or protecting the neurons of patients suffering from Parkinson's disease, the apamin is contained in bee venom.

In other words, whole bee venom may be used to provide the desired amount of apamin.

This is because bee venom is a well-controlled, natural product that is already used therapeutically for the desensitization of individuals allergic to bee venom.

However, especially, bee venom contains apamin in an amount of approximately 3% by weight, relative to the total weight of the bee venom.

The composition of the venom of *Apis mellifera*, the common European domestic bee, is reported in table I below:

TABLE I

| Class of compounds | Compounds | Percentage relative to dry weight |
|---|---|---|
| Enzymes | Phospholipase A2 | 10-12 |
| | Hyaluronidase | 1-2 |
| | Acid phosphomonoesterase | 1.0 |
| | α-D-glucosidase | 0.6 |
| | Lysophospholipase | 1.0 |
| Polypeptides | Melittin | 40-50 |
| | Melittin-F | 0.01 |
| | Apamin | 3 |
| | Mast cell degranulating peptide | 2 |
| | Secapin | 0.5 |
| | Tertiapin | 0.1 |
| | Protease inhibitor | — |
| | Procamine A and B | 1.4 |
| Low molecular weight compounds | Histamine | 0.66-1.6 |
| | Dopamine | 0.13-1 |
| | Noradrenaline | 0.1-0.7 |

This composition may vary, slightly, from one species of bee to the other.

Thus, the invention also relates to the use of bee venom, in an amount of between 33 micrograms and 330 micrograms, for the manufacture of a unit dose, for subcutaneous injection every one to six weeks, of a medicament for relieving the symptoms and/or restoring and/or protecting the neurons of patients suffering from Parkinson's disease.

In the same manner as for the use of apamin, the amount of bee venom to be used in the manufacture of this unit dose will depend on the patient to be treated and in particular on the weight of said patient.

This amount of bee venom is generally between 33 micrograms and 330 micrograms, limits included, preferably between 66 micrograms and 165 micrograms, most preferably from 100 to 110 micrograms, limits included.

The frequencies of injection of this unit dose are the same as for the unit dose containing apamin.

The invention will be understood more clearly and other advantages and characteristics thereof will emerge more clearly on reading the description which follows and which is given with reference to a nonlimiting and purely illustrative example.

EXAMPLE

A patient weighing 82 kilos, at an advanced Parkinsonian stage (15 years of disease) was treated, following an allergic reaction to bee venom, with a monthly injection of 110 micrograms of bee venom.

Following each injection, the motor score as determined on the Unified Parkinson's Disease Rating Scale (UPDRS III), improved by 70% in a few hours and then allowed said patient to completely eliminate the L-dopa treatment being received, for two to four weeks.

In any event, during the two weeks following the injection and preceding the next injection of bee venom, the treatment of said patient with L-dopa decreased by 50% compared with the period preceding the injection of bee venom.

This shows that apamin has an activity that is both symptomatic and neuroprotective, but especially that it has a neurorestorative activity in Parkinson's disease.

Of course, the unit dose containing apamin or bee venom can be used in combination with other therapies.

This unit dose of apamin or of bee venom may also be administered via a route other than the subcutaneous route. However, for reasons of availability of the total amount administered, the subcutaneous injection route remains preferred.

The invention claimed is:

1. A method for relieving a symptom, restoring neurons, and/or protecting neurons, of a patient suffering from Parkinson's disease, wherein the method comprises administering to the subject a therapeutically effective amount of apamin.

2. The method according to claim 1, wherein the therapeutically effective amount is 1-10 micrograms of apamin.

3. The method according to claim 1, wherein the therapeutically effective amount is 2-5 micrograms of apamin.

4. The method according to claim 1, wherein the therapeutically effective amount is 3-3.5 micrograms of apamin.

5. The method according to claim 1, wherein said administering comprises subcutaneous injection of apamin every one to six weeks.

6. The method according to claim 1, wherein said administering comprises subcutaneous injection of apamin once per week.

7. The method according to claim 1, wherein said administering comprises subcutaneous injection of apamin once every six weeks.

8. The method according to claim 1, wherein the apamin is administered in combination with another therapy.

9. The method according to claim 1, wherein the apamin is administered in combination with L-dopa.

10. The method according to claim 1, wherein the method is for relieving a symptom of a subject suffering from Parkinson's disease.

11. The method according to claim 1, wherein the method is for restoring neurons of a subject suffering from Parkinson's disease.

12. The method according to claim 1, wherein the method is for protecting neurons of a subject suffering from Parkinson's disease.

13. A method for treating Parkinson's disease, wherein the method comprises administering to a subject in need thereof a therapeutically effective amount of apamin.

14. The method according to claim 13, wherein the therapeutically effective amount is 1-10 micrograms of apamin.

15. The method according to claim 13, wherein the therapeutically effective amount is 2-5 micrograms of apamin.

16. The method according to claim 13, wherein the therapeutically effective amount is 3-3.5 micrograms of apamin.

17. The method according to claim 13, wherein said administering comprises subcutaneous injection of apamin every one to six weeks.

18. The method according to claim 13, wherein said administering comprises subcutaneous injection of apamin once per week.

---

SEQUENCE LISTING

```
<160> NUMBER OF SEQ ID NOS: 1

<210> SEQ ID NO 1
<211> LENGTH: 18
<212> TYPE: PRT
<213> ORGANISM: Apis mellifera

<400> SEQUENCE: 1

Cys Asn Cys Lys Ala Pro Glu Thr Ala Leu Cys Ala Arg Arg Cys Gln
1               5                   10                  15

Gln His
```

19. The method according to claim 13, wherein said administering comprises subcutaneous injection of apamin once every six weeks.

20. The method according to claim 13, wherein the apamin is administered in combination with another therapy.

21. The method according to claim 13, wherein the apamin is administered in combination with L-dopa.

22. A unit dose of a medicament for relieving a symptom, restoring neurons, and/or protecting neurons, of a patient suffering from Parkinson's disease, wherein the unit dose consists of a therapeutically effective amount of apamin in combination with L-dopa.

23. The unit dose according to claim 22, wherein the therapeutically effective amount is 1-10 micrograms of apamin.

24. The unit dose according to claim 22, wherein the therapeutically effective amount is 2-5 micrograms of apamin.

25. The unit dose according to claim 22, wherein the therapeutically effective amount is 3-3.5 micrograms of apamin.

26. The unit dose according to claim 22, wherein the therapeutically effective amount of apamin is administered by subcutaneous injection every one to six weeks.

27. The unit dose according to claim 22, wherein the therapeutically effective amount of apamin is administered by subcutaneous injection once per week.

28. The unit dose according to claim 22, wherein the therapeutically effective amount of apamin is administered by subcutaneous injection once every six weeks.

29. The unit dose according to claim 22, wherein the therapeutically effective amount of apamin is administered in combination with another therapy.

30. A unit dose of a medicament for treatment and/or prophylaxis of Parkinson's disease, wherein the unit dose consists of a therapeutically amount of apamin in combination with L-dopa.

31. The unit dose according to claim 30, wherein the therapeutically effective amount is 1-10 micrograms of apamin.

32. The unit dose according to claim 30, wherein the therapeutically effective amount is 2-5 micrograms of apamin.

33. The unit dose according to claim 30, wherein the therapeutically effective amount is 3-3.5 micrograms of apamin.

34. The unit dose according to claim 30, wherein the therapeutically effective amount of apamin is administered by subcutaneous injection every one to six weeks.

35. The unit dose according to claim 30, wherein the therapeutically effective amount of apamin is administered by subcutaneous injection once per week.

36. The unit dose according to claim 30, wherein the therapeutically effective amount of apamin is administered by subcutaneous injection once every six weeks.

37. The unit dose according to claim 30, wherein the therapeutically effective amount of apamin is administered in combination with another therapy.

* * * * *